(12) United States Patent
Clochard et al.

(10) Patent No.: US 9,134,267 B2
(45) Date of Patent: Sep. 15, 2015

(54) METHOD AND DEVICE USING NANOPOROUS MEMBRANE FOR DETECTING AND QUANTIFYING HEAVY METAL IONS IN A FLUID BY ANODIC STRIPPING VOLTAMMETRY

(75) Inventors: Marie-Claude Laurence Clochard, Sartrouville (FR); Travis Lee Wade, Paris (FR)

(73) Assignees: ECOLE POLYTECHNIQUE, Palaiseau (FR); COMMISSARIAT A L'ENERGIE ATOMIQUE ET AUX ENERGIES ALTERNATIVES, Gif sur Yvette (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 630 days.

(21) Appl. No.: 12/996,141

(22) PCT Filed: Jun. 5, 2009

(86) PCT No.: PCT/EP2009/056967
§ 371 (c)(1),
(2), (4) Date: Mar. 7, 2011

(87) PCT Pub. No.: WO2009/147244
PCT Pub. Date: Dec. 10, 2009

(65) Prior Publication Data
US 2011/0186449 A1 Aug. 4, 2011

(30) Foreign Application Priority Data

Jun. 6, 2008 (EP) ..................... 08305237

(51) Int. Cl.
*G01N 27/42* (2006.01)
*G01N 27/40* (2006.01)
(Continued)

(52) U.S. Cl.
CPC ............... *G01N 27/31* (2013.01); *G01N 27/40* (2013.01); *G01N 27/42* (2013.01); *G01N 33/18* (2013.01); *G01N 33/1813* (2013.01); *G01N 27/333* (2013.01)

(58) Field of Classification Search
CPC . G01N 27/31; G01N 27/333; G01N 27/3335; G01N 27/40; G01N 2030/527; G01N 33/1813
USPC .......................................... 204/415; 205/793
See application file for complete search history.

(56) References Cited

U.S. PATENT DOCUMENTS 4,024,766 A * 5/1977 Perry .......................... 73/864.35
4,956,219 A * 9/1990 Legras et al. .................. 343/771
(Continued)

FOREIGN PATENT DOCUMENTS

WO 2005033685 A 4/2005
WO 2006120396 A 11/2006

OTHER PUBLICATIONS

Yantasee et al. Anal. Chim. Acta 502, 2004, 207-212.*
(Continued)

*Primary Examiner* — Alex Noguerola
*Assistant Examiner* — Steven Rosenwald
(74) *Attorney, Agent, or Firm* — Young & Thompson

(57) ABSTRACT

Method and a device for capturing heavy metal ions included in sewage sludge. The method includes steps of:
a) placing in the fluid a functionalized radiografted track-etched membrane FRTEM which contains polymer nanopores; this membrane including a first electrode on one side of the membrane,
b) selectively capturing heavy metal ions inside the polymer nanopores,
c) applying an anodic stripping voltammetric ASV analysis on the membrane in order to differentiate and quantify captured metal ions, the first electrode being used as an ASV detection electrode.

21 Claims, 5 Drawing Sheets

(51) Int. Cl.
  *G01N 33/18* (2006.01)
  *G01N 27/31* (2006.01)
  *G01N 27/333* (2006.01)

(56) References Cited

U.S. PATENT DOCUMENTS

2006/0275859 A1* 12/2006 Kjaer ............................. 435/25
2007/0048745 A1   3/2007 Joyce et al.

OTHER PUBLICATIONS

Siwy et al. Appl. Phys. A 76, 781-785, 2003.*
Cuscito et al. Physics Research B, 265, 2007, 309-313.*
Bard and Faulkner; Electrochemical Methods: Fundamentals and Applications, 1980, John Wiley and Sons, pp. 413-420.*
Sonthalia et al. Anal. Chim. Acta 522, 2004, 35-44.*
Cuscito et al, "Nanoporous beta-PVDF membranes with selectively functionalized pores", Nuclear Instruments & Methods in Physics Research, Section—B: Beam Interactions With Materials and Atoms, Nov. 17, 2007, pp. 309-313, vol. 265, No. 1, Elsevier, Amsterdam, NL, XP022349433.
Dauginet-De Pra L et al: "Fabrication of a new generation of track-etched templates and their use for the synthesis of metallic and organic nanostructures" Nuclear Instruments & Methods in Physics Research, Section—B: Beam Interactions With Materials and Atoms, Nov. 1, 2002, pp. 81-88, vol. 196, No. 1-2, Elsevier, Amsterdam, NL, XP004391363.
Martin C R et al: "Nanomaterials", Analytical Chemistry, American Chemical Society, May 1, 1998, pp. 322A-327A, vol. 70, Columbus, US, XP009009266.
International Search Report, dated Oct. 13, 2009, in PCT/EP2009/056967.
European Search Report, dated Oct. 10, 2008, in EP 08 30 5237.

* cited by examiner

METHOD AND DEVICE USING NANOPOROUS MEMBRANE FOR DETECTING AND QUANTIFYING HEAVY METAL IONS IN A FLUID BY ANODIC STRIPPING VOLTAMMETRY

BACKGROUND OF THE INVENTION

1. Field of the Invention

The invention relates to nanosensors, and more particularly, to a method and device for detecting and quantifying charged molecules and favourably heavy metal ions in a fluid. The present invention advantageously applies to sewage sludge, but it could apply to biological or medical fields. It could also apply to the detection of other ionic species in fluid, not only heavy metal ions.

2. Description of the Related Art

The urban wastewater collection is one of the main facilities used for the disposal of commercial and domestic wastes, both of which may contain heavy metals. Wastewater treatment processes are generally effective in limiting the discharge of potentially toxic elements to the aquatic environment because a high proportion of the contaminant load is extracted and concentrated in the sewage sludge. Application of sewage sludge to agricultural land is the largest outlet for its beneficial use, and this is consistent with EC policy on waste recycling, recovery, and use. The Sewage Sludge Directive 86/278/EEC sets upper limits of trace metals in municipal sewage sludge for use on agricultural land, and revision of the directive is expected to lead to even more stringent limits. This is a critical issue due to the increasing amount of sludge produced (from 5.5M tonnes of dry matter in 1992 to 9M tonnes in 2005), and the fact that other alternatives (incineration and landfill) are not generally considered environmentally acceptable. Consequently, wastewater sludge quality must be protected and improved in order to secure the agricultural outlet as the most cost effective as sustainable solution.

The most widespread method for the determination of metal concentrations in wastewaters is via grab sampling and subsequent laboratory analysis. This method is both expensive, which limits its application, and time consuming, which means that pollution events can be missed, or detected too late. In the face of increasing levels of sludge production, the expected application of more stringent limits on heavy metal concentrations in sludge, and to identify, survey, and control the sources of input of toxic elements, there is a need for a low cost, time effective, easy to handle and very sensitive analysis system to determine the concentration of heavy metals in waste waters.

In addition, existing sensors to detect metal residues present following drawbacks:
- metal-based screen-print electrodes or modified glassy carbon are not accurate enough to detect residue (detection limits of 0.5, 2.0, 0.9 and 1.4 µg/L),
- most of them suffer from analyte peak distortion, peak overlap, and loss of sensitivity due to interference of analyte ions with each other,
- Hg film coated electrodes are accurate enough at ppt levels (ng/L) by ion pre-concentration but not environmentally friendly.

SUMMARY OF THE INVENTION

An object of the present invention is to overcome drawbacks of prior art by providing a new, low cost, and rapid method to diagnose traces of heavy metal residues in sludge and treated wastewater. Another object of the present invention is a new nanosensor reusable which permits an efficient screening.

In at least preferred embodiments, the present invention provides a method for capturing charged molecules and favourably heavy metal ions included in a fluid, said method comprising steps of:

a) placing in the fluid a functionalised radiografted track-etched membrane FRTEM which contains polymer nanopores; this membrane comprising a first electrode on one or both sides of the membrane, b) selectively capturing charged molecules inside the polymer nanopores, without the need to apply a potential, c) applying an anodic stripping voltammetric ASV analysis on the membrane in order to differentiate and quantify captured charged molecules, said first electrode being used as an ASV detection electrode.

With the present invention, it is possible to rapidly monitor the efficiency of a fluid treatment. The present invention provides a new low cost and time effective nanosensor which is able to diagnose traces of heavy metal residues in for example sewage sludge and treated wastewater by absorption. In other words, after a calibrated period of time (from seconds to around 15 minutes for example) in which the capturing step b) is carried out notably without an applied potential, the charged molecules are selectively concentrated inside the polymer nanopores due to functionalisation of the nanopores. The first electrode permits then an efficient screening and rapid measurement of trace levels of the trapped charged molecules by anodic stripping voltammetry ASV methods. More generally, depending on the specific functionalisation of the nanopores, this nanosensor is useful for the analysis of biological or medical samples or any of the analysis that is performed by anodic stripping voltammetry such as those of screen-printed electrodes and other stripping voltammetry techniques such as cathodic stripping voltammetry (CSV) or adsorbtive stripping voltammetry (AdSV).

Preferably, the polymer nanopores consist in tubules through the entire thickness of the membrane. The membrane could be in the shape of a cylinder or parallelepiped in which tubules are all parallel and perpendicular to the two opposite sides of the membrane. The thickness of the membrane could substantially be of 9 µm and the nanopores could present a diameter between 20 and 100 nm. Moreover, each side of the membrane could present surface area of substantially 400 $mm^2$.

Advantageously, nanoporous membranes according to the present invention would have better diffusion profiles than porous sponge like films due to 2D diffusion as opposed to 3D diffusion, such as glassy carbon, and an uniform distribution of pore diameter and length.

In preferred embodiment, the membrane is specifically grafted inside the nanopores. The synthesis of functionalized radio grafted membranes comprises notably steps of irradiation to activate radicals, chemical etching and radiografting. The remanence of the radicals within the nanopore walls after etching allows one to radiograft specifically inside the nanopores and not on the membrane surface. Under wastewater streams, for example, the functionalised radiografted, track-etched membrane (FRTEM) can thus trap cations and concentrate them.

According to a preferred embodiment of the invention, for capturing charged molecules in step b), the membrane is kept fixed under a fluid flow. According to a variant of the invention, for capturing charged molecules in step b), the membrane could be kept moving in the fluid or in a quiescent fluid.

According to an embodiment of the invention, the membrane is based on a poly(vinylidenefluoride) PVDF film which can be radiografted with vinyl monomers. In other words, in the presence of vinyl monomer, such as acrylic acid (AA), a radical polymerization takes place by radiografting to specifically functionalise the nanopore wall with hydrogel.

Advantageously, the membrane comprises a second electrode on another side of the membrane. Thus, in step c), the first and second electrodes can be connected together. They both serve as working electrodes during the ASV analysis or the other side of the membrane could function as the counter electrode.

According to a variant embodiment of the invention, the first and second electrodes can be held at different negative potentials. For example, in step c), the first electrode can be held at a fixed negative potential to collect charged molecules of interest; the second electrode being held at a potential negative enough to deposit interfering charged molecules but less negative than said fixed negative potential enough not to deposit charged molecules on interest. The second electrode acts as a charged molecule filter and extends the sensitivity and utility of the membrane.

According to the invention, each electrode is made by sputtering metallic or conducting particles, like carbon, respectively on each side of the membrane in such a way that the nanopores remain open. Each electrode can be a layer of gold or any other metallic or conducting material.

Preferably, during step a), the membrane is covered with a waterproof tape, such as Kapton, in which an aperture is realised to serve as a window for exposure of the membrane to the fluid.

In another aspect, the invention also enables the provision of a new device or nanosensor for capturing charged molecules and favourably heavy metal ions included in a fluid; said device comprising a functionalised radiografted track-etched membrane FRTEM which contains polymer nanopores; this membrane comprising a first electrode on one side of the membrane, the first electrode being designed to serve as an ASV detection electrode.

The nanosensor according to the invention is accurate from pre-concentration without applying a potential or without using any Hg, is low cost, reusable, and has better peak definition and separation due to charged molecules screening and filtering. The lack of necessity to apply a potential for pre-concentration is a distinct advantage over Hg electrodes or screen printed electrodes.

BRIEF DESCRIPTION OF THE DRAWING FIGURES

For the purpose of illustrating the invention, there is shown in the drawings a form that is presently preferred; it being understood, however, that this invention is not limited to the precise arrangements and instrumentalities.

Figure 4:
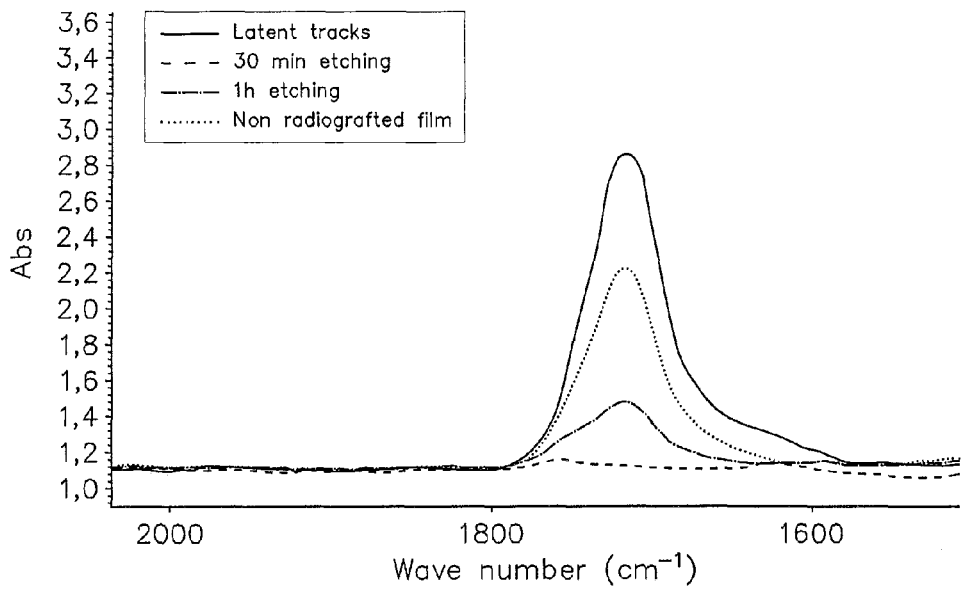
Figure 5:
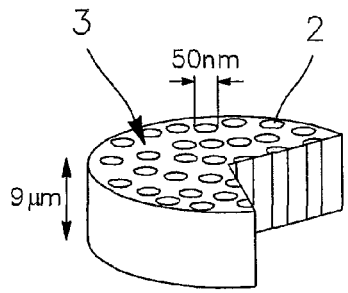
Figure 6:
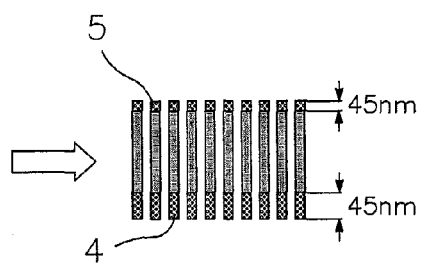
Figure 7:
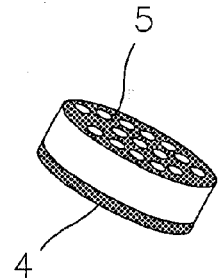
Figure 8:
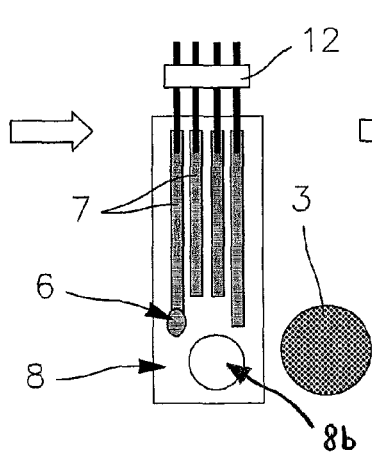
Figure 9:
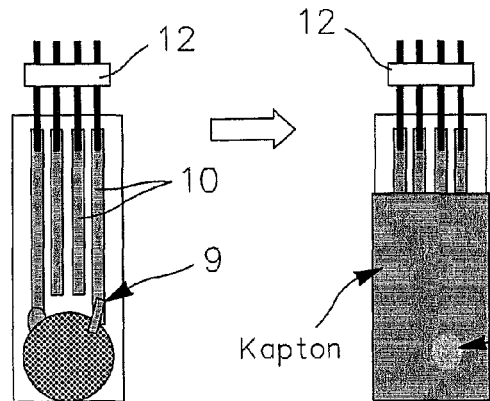
Figure 10:
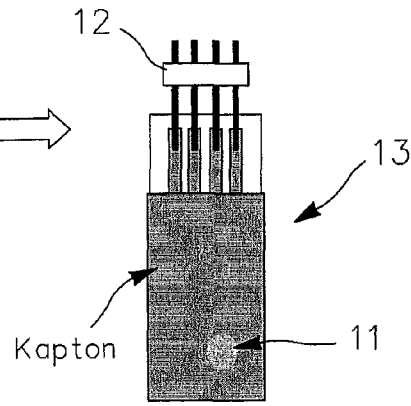
Figure 11:
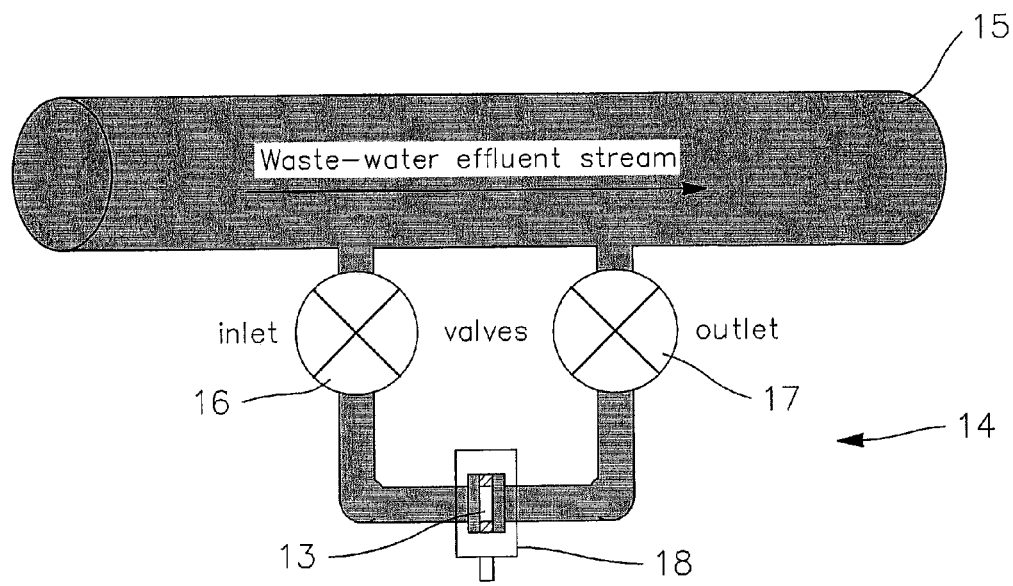
Figure 12:
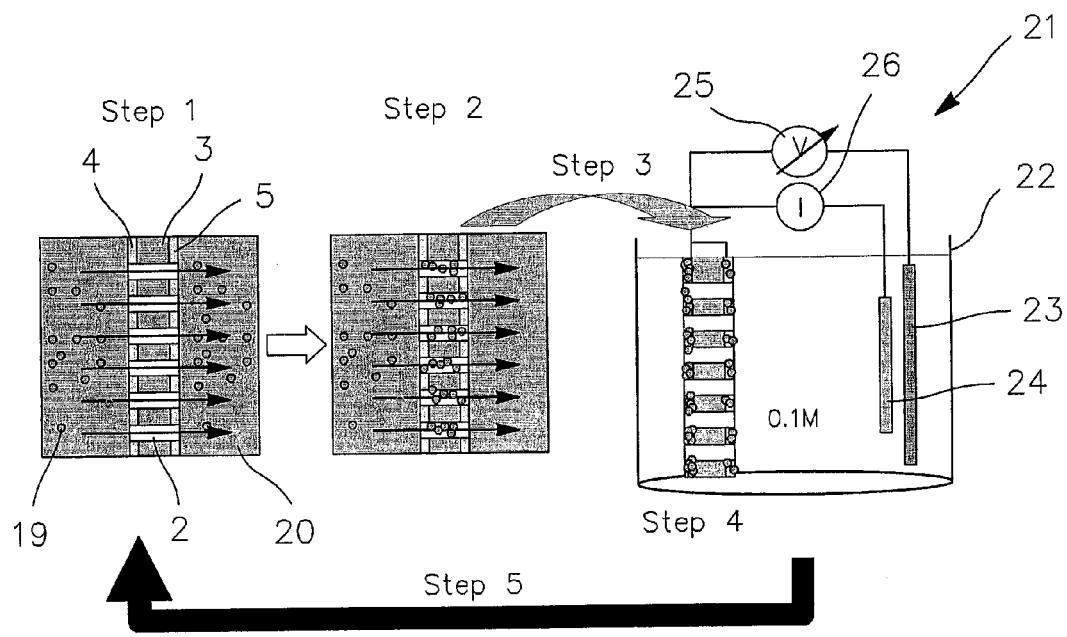
Figures 13, 14, 15:
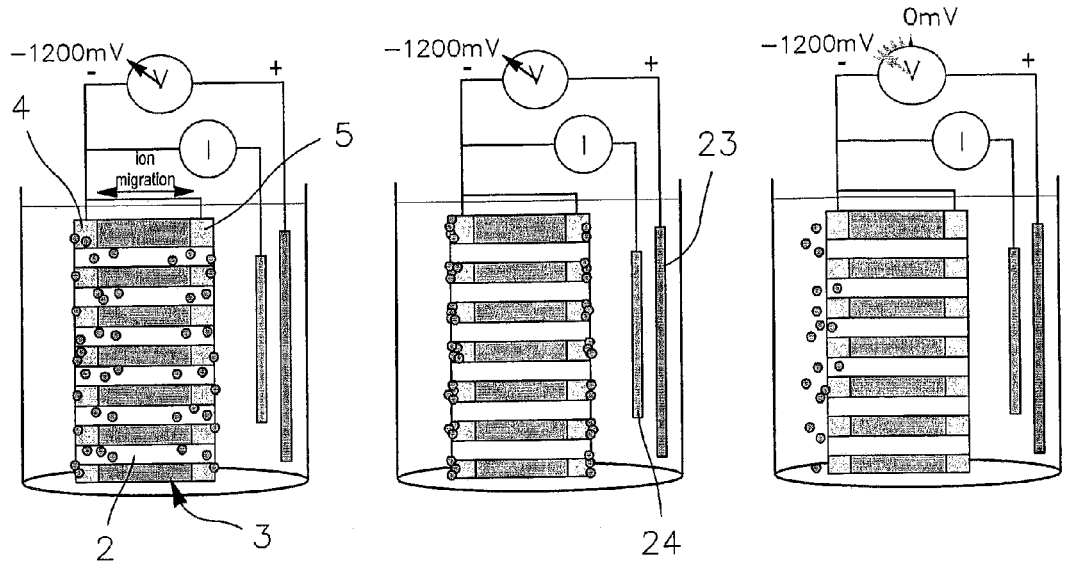
Figure 16:
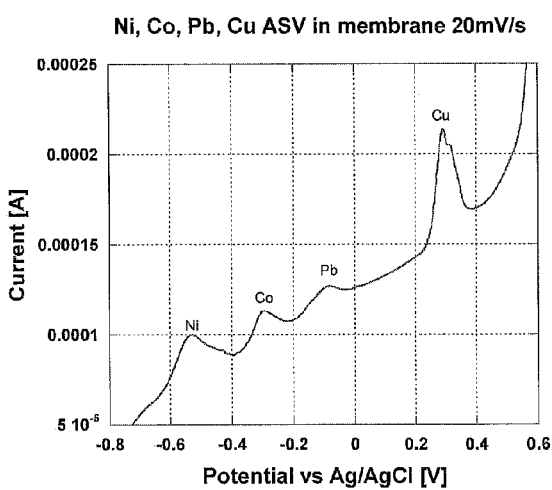

FIG. 4 is a graph illustrating a FTIR spectra of swift heavy ion $_{58}Ni^{25+}$ irradiated PVDF-g-PAA for different etching times (AA concentration 100% v/v, fluence $10^9\,cm^{-2}$, Mohr's salt 0.25% w/w, radiografting at 60° C. for 1 hour); the maximum corresponds to O—C=O stretching (1701 $cm^{-1}$) and gives evidence of COOH groups radiografted PAA chains;

FIG. 5 is a schematic view of a membrane cut in order to view nanopore walls;

FIG. 6 shows a schematic cut-away side view of a membrane with gold electrodes on top and bottom sides;

FIG. 7 shows a perspective view of the membrane of FIG. 6;

FIGS. 8-10 are schematic views illustrating the insertion of the membrane onto a membrane-holder constituting a nanosensor;

FIG. 11 is a schematic view illustrating a nanosensor according to the invention disposed in a detour of a wastewater effluent pipe;

FIG. 12 shows several schematic views illustrating successive steps of use of a reusable membrane, after the complete analysis of FIGS. 13-15 the membrane is ready for reuse;

FIG. 13-15 shows schematic views illustrating ASV analysis on a membrane according to the invention;

FIG. 16 is a graph of an ASV response of a solution containing 1 mM each of Ni(II), Co(II), Pb(II), and Cu(II) using an immersion time of 60 s and a deposition potential of $-1200$ mV (vs. Ag/AgCl).

Figure 17:
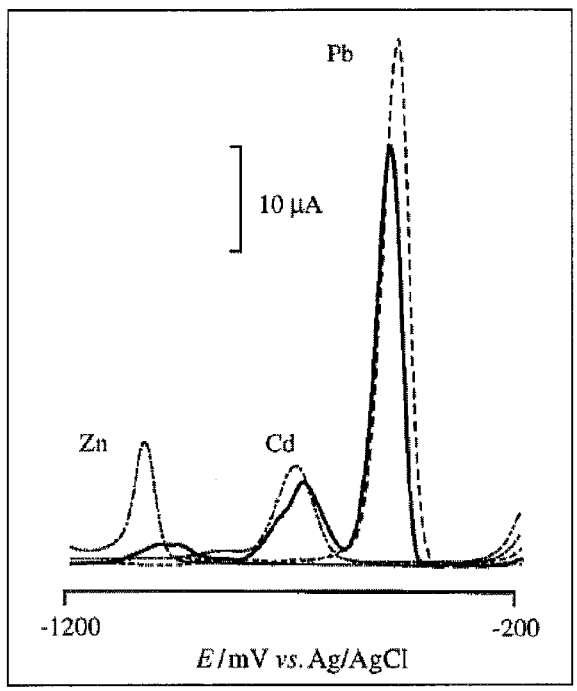

FIG. 17 is a graph from Santos J. H. et al Anal. Commun. 35 (1998) 345-348 illustrating a DPASV response of a solution containing 50 uM each of Pb(II), Cd(II), and Zn(II) using an immersion time of 60 s and a deposition potential of $-1200$ mV (vs Ag/AgCl); superimposed curves are those taken using single metal solutions and a blank.

Figure 18:
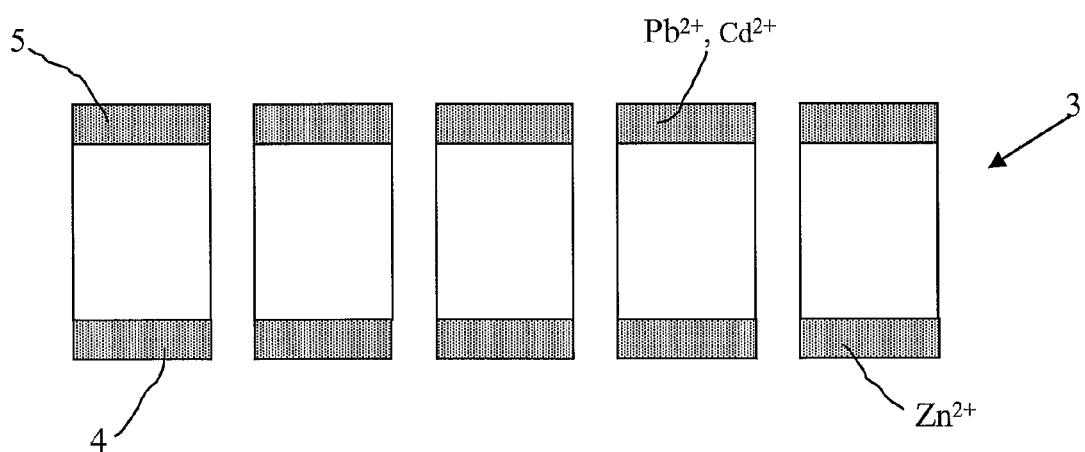

FIG. 18 is a schematic view of a nanosensor in which one electrode of the membrane is used as a filter or a screening electrode.

DETAILED DESCRIPTION OF THE INVENTION

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

In accordance with the preferred embodiment, the method and device according to the invention relates to the following materials and processes:

Materials:

Poly(vinylidenefluoride) (PVDF) films of 9 µm thickness provided by PiezoTech SA®, Saint Louis (France). Toluene, potassium hydroxide, potassium permanganate, potassium disulfite, acrylic acid (AA), Mohr's salt (($NH_4$)$_2$Fe($SO_4$)$_2$.6$H_2O$), sulphuric acid, EDC($C_8H_{17}N_3$.HCl), phosphate buffer saline (PBS) and Alexa Fluor R 488 hydrazide (C21H15N4NaO10S2) purchased from Invitrogen®.

Irradiation:

Prior to irradiation, PVDF films are toluene-extracted for 24 h. Swift heavy ion irradiation was performed at the GANIL, Caen (France). Films are irradiated with Kr ions (10.37 MeV/amu, fluence $10^7$ to $10^{10}\,cm^{-2}$) under He atmosphere. In two cases, samples are stored at $-20°$ C. under $N_2$ atmosphere until chemical etching and radiografting.

Chemical Etching:

PVDF irradiated films are chemically etched using permanganate solution (0.25 M) in a highly alkaline medium (KOH 10 M) at 65° C. with different etching times from 0.5 to 3 h. Membranes obtained are washed in potassium disulfide solution (15%) then dried at 50° C. under vacuum.

Radiografting:

PVDF films of initial size 20×20 mm$^2$, are weighed. The film was immersed at room temperature in a radiografting solution containing acrylic acid and Mohr's salt (0.25% w/w). After 15 minutes of bubbling nitrogen at room temperature, the sample is introduced into a thermostated water bath at 60° C. for 1 hour. Membranes are washed with water and then Soxhlet-extracted in boiling water in order to extract free homopolymer. Functionalised membranes are dried at 50° C. under vacuum.

Infra-Red Spectroscopy:

FTIR spectra of PVDF films are obtained with a Nicolet Magna-IR 750 spectrometer equipped with a DGTS detector. Spectra are recorded in an attenuated total reflection mode (ATR) using a diamond-crystal with single reflection. Spectra are collected by accumulating 32 scans at a resolution of 2 cm$^{-2}$.

Confocal Scanning Laser Microscopy (CSLM):

Measurements are performed at LLB (CEA-Saclay, France) with a Leica TCS-SP2 using an Ar laser (488 nm). Samples are observed in water with a 40× dry objective of numerical aperture 0.85.

Electrode Fabrication, as Shown on FIGS. 5-10:

A first gold bottom layer, ~45 nm is sputtered (EMITECH K550, UK) through a mask with 3 mm diameter holes. Next, a second gold layer, ~45 nm, is sputtered, through a mask, on the other side of the membrane over the same areas as the first gold area.

Anodic Stripping Voltametry (ASV):

Electrochemical quantification of trace metal analytes is done by ASV. This involves the electrochemical reduction of the concentrated metal ions from the membrane on a metal coating on the surface of the membrane, which is the working electrode of an electrochemical cell. The electrode is held at a very negative potential, which reduces all of the trapped metal ions to their metallic, zero valence, state. The electrode is then scanned slowly toward positive potentials where the ions are oxidized, anodically stripped, and the resulting current is proportional to the concentrations of the ions trapped in the membrane. Different metals oxidize at different potentials so the kind of metal can be identified. The analysis is performed with a potentiostat (HEKA PG310, Germany) with a Ag/AgCl (Metrohm, Switzerland) reference electrode.

The synthesis of functionalized radio grafted membranes is described according to FIGS. 1-4. With respect to FIG. 1, a track-etch process is described. This process comprises three steps:

I) latent track formation along the ion pathway through a polymer film 1,

II) symmetrical attack of latent tracks by hydrolysis at early stage of the process, and III) formation of cylindrical pores 2.

In other words, for the preparation of a functionalised radio grafted track-etched membrane 3 (FRTEM), polymer film 1 is first bombarded by swift heavy ions and the formed tracks along the ion passage are revealed under alkaline chemical treatment.

The obtained nanoporous polymer membrane 3 does not need to undergo a subsequent e-beam irradiation to increase radical proportion in polymer bulk submicronic pore diameter. Indeed, after etching times inferior to one hour, the radical residues within nanopore walls were found sufficiently numerous to persue a radiografting from the pore walls 2.

Figure 1:
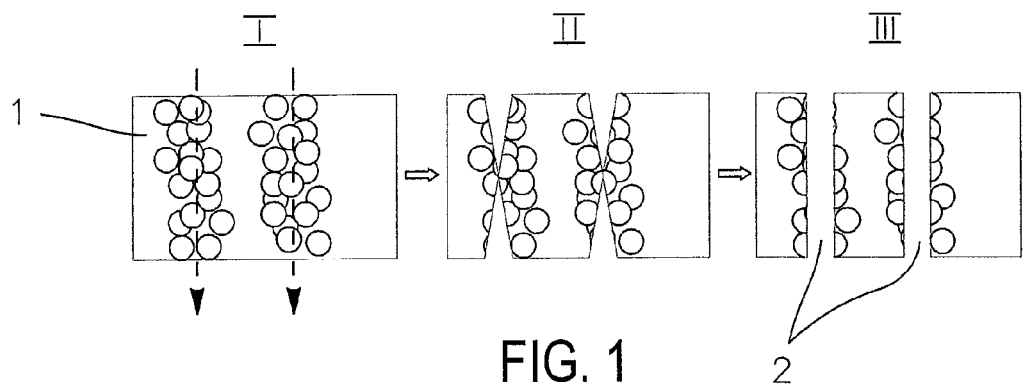
FIG. 1 is a schematic view illustrating Track-etch process: I) Swift Heavy Ions irradiation forms damaged zones in the polymer bulk along the ion pathway called latent tracks, II) the latent tracks are chemically etched forming nanopores of biconical shape at the early stage and III) if the track etch rate is sufficiently higher than the bulk etch rate, biconical nanopores become cylindrical.
Figure 2:
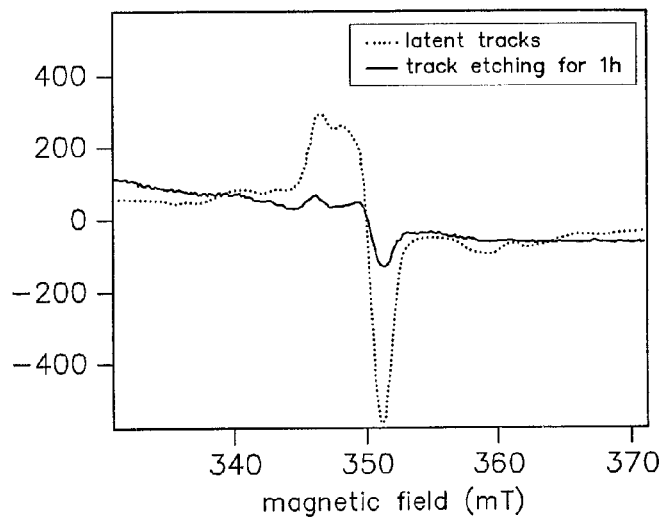
FIG. 2 is a graph illustrating the electron paramagnetic resonance (EPR) spectra per mass unit ($mg^{-1}$) for a heavy ion irradiated film.
Figure 3:
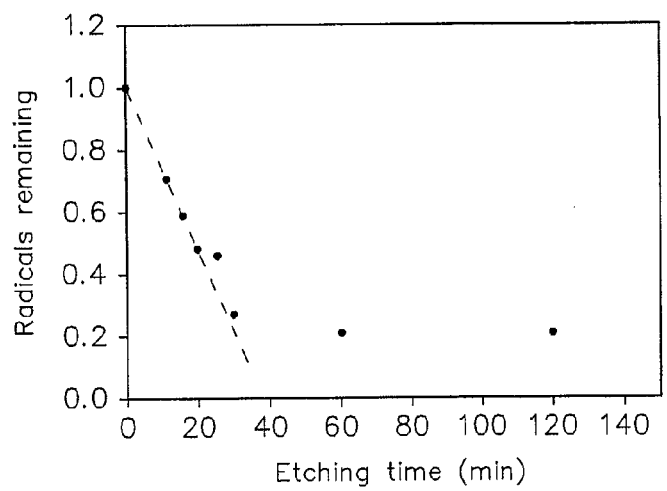
FIG. 3 is a graph illustrating the radical decay from EPR results versus time.

FIG. 2 shows an electron paramagnetic resonance (EPR) spectra per mass unit (mg$^{-1}$) for a heavy ion irradiated film before etching (latent tracks) and after 1 hour of track etching. In the latter case, the non-horizontal baseline is due to paramagnetic impurities (KMnO$_4$ from the etching bath). FIG. 3 shows the radical decay from EPR results versus time. Radicals are always presents even after 1 hour of track etching.

Concerning the functionalisation, in the presence of vinyl monomer, such as acrylic acid (AA), a radical polymerization takes place by radiografting process to specifically functionalise the nanopore walls with carboxylate hydrogel as shown from FTIR spectra in FIG. 4. This polymerization is specific to the nanopore walls and does not occur on the membrane surface. The selectivity of the grafting is checked by labelling of the amine pre-functionalised surface of the PVDF nanoporous membrane by a fluorescent probe specific to the amines and the poly(acrylic acid) inside the pores by a second fluorescent probe specific to the acid groups.

The carboxylate hydrogel located inside the nanopores is able to form complexes with metal ions. In order to improve its cation affinity, it is possible to functionalise it by common coupling reactions with a chelating molecule (eg. Mono- and polyacides, mono and polyamines, Ethylene Diamine Tetra Acetate and derivatives, cyclodextrines, crownethers or any clathrates complexes). Chelation ("chélation" in French) is the binding or complexation of a bi- or multidentate ligand. These ligands, which are often organic compounds, are called chelants, chelators, chelating agents, or sequestering agent. These molecules should have a very important chelating power to trap even more effectively the heavy metal ions.

Turning now to FIGS. 5-10, a nanosensor 13 according to the invention is shown. The nanosensor is based on the membrane 3, the shape of which is a cylinder of 9 µm thick and of 400 mm$^2$ surface area, with 106 to 1010 nanopores per cm$^2$ of 50 nm diameter. Once the membrane has been functionalised, gold is sputtered on each side of the membrane 3 in FIG. 6: a bottom electrode 4 of 45 nm thick and a top electrode 5 of 45 nm thick. The sputtering is made in such a way that the nanopores remain open. The gold layers can cover or not the entire side surface. On FIG. 7 the perspective view of the membrane shows the top electrode 5 and the bottom electrode 4. On FIGS. 8-10, the bottom layer 4 is contacted with silver paste 6 to copper contacts 7 lithographically patterned on 1.5 cm$^2$ plexiglass plackets 8 with a 4 mm diameter hole, 8b. The top layer 5 is contacted with a gold wire 9 and silver paste to other copper contacts 10 on the same placket 8. The membrane 3 is then covered with waterproof tape, Kapton, 3M, except for a 2 mm diameter circular area 11 in the centre of the membrane, which will serve as a window for exposure of the membrane to the wastewater. The copper leads are not completely covered by the tape and remain outside of the solution so they can be connected to a potentiostat via a bridge 12.

The nanosensor 13 according to the present invention is very compact and easy to handle.

The nanosensor 13 can then be immersed into wastewater for a preset time to absorb ions based on calibration. According to an embodiment of the invention, the nanosensor could be used by placing it in a small detour 14 of a waste-water effluent pipe 15 as shown on FIG. 11. The detour 14 comprises an inlet pipe equipped with an inlet valve 16, and an outlet pipe equipped with an outlet valve 17. Between said valves, is disposed the nanosensor 13 inside a sealed nanosensor closure 18.

FIG. 12 shows possible steps of the nanosensor 13 employment, for simplification membrane 3 alone is shown:
- step 1: membrane 3 immersion under treated waste-water flow or sludge 20, the heavy metal ions 19 pass through nanopores 2 of the membrane 3,
- step 2: heavy metal ion trapping/concentration effect,
- step 3: membrane 3 removal, rinsing and immersion into a voltammetric cell 21 comprising a cell body 22 housing a reference Ag/AgCl electrode 23 and a counter gold electrode 24, the top electrode 4 and bottom electrode 5 are connected together and act as a working electrode of the voltammetric cell. A controllable voltmeter 25 is disposed in series between the reference electrode 23 and the working electrode 4, 5. An ammeter 26 is disposed in series between the counter electrode 24 and the working electrode 4, 5. The voltmeter and ammeter together are referred to as the potentiostat.
- step 4: heavy metal ions reduced onto one or both gold layers 4, 5 as working electrodes by a negative potential then anodically stripped and analysed,
- step 5: membrane 3 ready for redeployment.

FIGS. 13-16 show detailed scheme of the electrochemical ASV analysis from step 4. On FIG. 13, the heavy metal ions migrate to one or both electrodes 4, 5 by a negative potential −1200 mV applied between the reference electrode 23 and the gold electrodes 4, 5. On FIG. 14, the ions are then reduced onto the electrodes 4, 5 at the potential of −1200 mV. On FIG. 15, the potential is then scanned in a positive sense from −1200 mV to −200 mV, which oxidizes (dissolves) the heavy metal ions into solution (anodic stripping voltammetry). On FIG. 16, the resulting current intensity and position, measured between the electrodes 4, 5 of the membrane 3 and the counter electrode 24, indicate the type and concentration of the heavy metal ions The resulting currents are proportional to the contaminate ions concentration based on previous calibration.

FIG. 16 is a plot of an ASV response from a solution containing 1 mM (1 ppm) each of Ni(II), Co(II), Pb(II), and Cu(II) using an immersion time of 60 s and a deposition potential of −1200 mV (vs Ag/AgCl) then stripped at 20 mV/s.

FIG. 17—from Santos J. H. et al Anal. Commun. 35 (1998) 345-348—illustrates, in continuous line, a differential-pulse anodic stripping voltammetry DPASV response of a solution containing 50 µM each of Pb(II), Cd(II), and Zn(II) using an immersion time of 60 s and a deposition potential of −1200 mV (vs. Ag/AgCl). The superimposed curves are those taken using single metals and a blank. It is clearly seen that when the three metals are analysed from the same solution there is interference that reduces the quality of the signal especially for Zn(II). The plots for the solutions with only one contaminant ion have large, well-defined currents. However, the plot for the solution with all three ions shows a decrease in the current maxima due to peak broadening and a shift in peak positions, especially for the $Zn^{2+}$ and $Cd^{2+}$ ions. This is due to the fact that it is more difficult for the Zn to be anodically stripped with the Pb and Cd on the surface. In order to overcome this drawback, the present invention provides an embodiment in which the top electrode 5 is never connected to the bottom electrode 4.

This embodiment provides thus two independent electrodes 4 and 5, one 4 on the bottom for detecting the ions of interest, detection electrode, and one 5 on the top to remove interfering ions by holding it at a potential negative enough to deposit the interfering ions but positive enough not to deposit the ions of interest, screening or filter electrode. FIG. 18 shows such an embodiment in which, the top electrode 5 is held at −800 mV where the Pb and Cd ions would be cathodically collected onto electrode 5 without the Zn ions and next, the bottom electrode 4 is held at −1200 mV to independently collect the Zn ions. The Zn could be anodically stripped to measure its concentration without interference from the other ions. With this scheme there are fewer problems due to interference from other ions and thus lower detection limits. The ability to play with the potential of the two independent electrodes makes this nanosensor very versatile.

With the nanosensor according to the invention, the pore length, diameter, and density can be chosen. The membrane specificity can be chosen by the type of functionalisation of the nanopore walls. The membrane may also be designed not only sensor but as a kit to screen several chelatant molecules. And it can be made specific for other ions and/or molecules based on the chelatant molecules. The functionalized membrane has the ability to trap and concentrate ions for analysis without the application of a potential unlike Hg or screen-printed electrodes.

Numerous variations and modifications will become apparent to those skilled in the art once the above disclosure is fully appreciated. It is intended that the following claims be interpreted to embrace all such variations and modifications.

The invention claimed is:

1. A method for detecting and quantifying charged molecules or heavy metal ions in a fluid, said method comprising steps of:
   a) placing in the fluid a membrane containing polymer nanopores, the nanopores having been functionalized by being formed from a radiografted track-etched polymer, a first non-functionalized electrode being on one side of the membrane;
   b) selectively capturing charged molecules or heavy metal ions inside the polymer nanopores without applying a potential;
   c) applying a negative potential to the first electrode to migrate the captured charged molecules or heavy metal ions to said first electrode; and
   d) applying an anodic stripping voltammetric analysis on the membrane in order to differentiate and quantify captured charged molecules or heavy metal ions, said first electrode being used as an anodic stripping voltammetric detection electrode.

2. The method according to claim 1, wherein the polymer nanopores are in tubules through the entire thickness of the membrane.

3. The method according to claim 1, wherein the membrane is specifically grafted inside the nanopores.

4. The method according to claim 1, wherein the membrane is based on a poly(vinylidenefluoride) film.

5. The method according to claim 4, wherein the poly(vinylidenefluoride) film is radio grafted with vinyl monomer and chelating molecule leading to a polymerization of nanopores walls.

6. The method according to claim 1, wherein a second electrode is on another side of the membrane.

7. The method according to claim 6, wherein, in step d), the first and second electrodes are connected together.

8. The method according to claim 1, wherein the first and second electrodes are held at different negative potentials.

9. The method according to claim 8, wherein in step d), the first electrode is held at a fixed negative potential to collect charged molecules of interest; the second electrode being held at a potential negative enough to deposit interfering charged molecules but higher than said fixed negative potential enough not to deposit charged molecules on interest.

10. The method according to claim 1, wherein the first electrode is made by sputtering metallic or conducting particles on one side of the membrane in such a way that the nanopores remain open.

11. The method according to claim 1, wherein the first electrode is a layer of gold or conducting film.

12. The method according to claim 1, wherein for capturing charged molecules in step b), the membrane is kept fixed under a fluid flow.

13. The method according to claim 1, wherein for capturing charged molecules in step b), the membrane is kept in a quiescent fluid or the membrane is kept moving in the fluid.

14. The method according to claim 1, wherein the capturing step b) is carried out during a calibrated period of time.

15. The method according to claim 1, wherein during step a), the membrane is covered with a waterproof tape in which an aperture is realised to serve as a window for exposure of the membrane to the fluid.

16. The method according to claim 1, wherein the fluid is a sewage sludge.

17. The method according to claim 1, wherein during step a), the membrane is placed in a detour of a wastewater effluent pipe.

18. The method according to claim 1, wherein a thickness of the membrane is about 9 µm and the nanopores present a diameter between 20 and 100 nm.

19. The method according to claim 1, wherein each side of the membrane has a surface area of about 400 $mm^2$.

20. The method according to claim 6, wherein the second electrode is made by sputtering metallic or conducting particles on one side of the membrane in such a way that the nanopores remain open.

21. The method according to claim 20, wherein the first electrode or the second electrode is a layer of gold or conducting film.

* * * * *